United States Patent
Taylor (10) Patent No.: US 8,104,483 B2
(45) Date of Patent: Jan. 31, 2012

(54) MULTI-PORT LIGHT DELIVERY CATHETER AND METHODS FOR THE USE THEREOF

(75) Inventor: Kevin D. Taylor, Colorado Springs, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 942 days.

(21) Appl. No.: 11/616,214

(22) Filed: Dec. 26, 2006

(65) Prior Publication Data

US 2008/0154345 A1 Jun. 26, 2008

(51) Int. Cl.
*A61B 19/00* (2006.01)
(52) U.S. Cl. ............................ 128/898; 606/7; 606/15
(58) Field of Classification Search ............... 606/7, 15; 607/88, 89; 128/898
See application file for complete search history.

(56) References Cited

U.S. PATENT DOCUMENTS

| | | | |
|---|---|---|---|
| 4,217,904 A | 8/1980 | Zahorsky | |
| 4,641,912 A | 2/1987 | Goldenberg | |
| 4,732,448 A | 3/1988 | Goldenberg | |
| 4,735,606 A | 4/1988 | Davison | |
| 4,748,982 A | 6/1988 | Horzewski et al. | |
| 4,772,268 A | 9/1988 | Bates | |
| 4,794,931 A | 1/1989 | Yock | |
| 4,799,754 A | 1/1989 | Goldenberg | |
| 4,830,460 A * | 5/1989 | Goldenberg | 385/118 |
| 4,834,093 A | 5/1989 | Littleford et al. | |
| 4,842,582 A | 6/1989 | Mahurkar | |
| 4,844,062 A | 7/1989 | Wells | |
| 4,899,363 A | 2/1990 | Murray et al. | |
| 4,919,508 A | 4/1990 | Grace et al. | |
| 4,961,809 A | 10/1990 | Martin | |
| 4,998,794 A | 3/1991 | Holzman | |
| 5,024,234 A | 6/1991 | Leary et al. | |
| 5,054,492 A | 10/1991 | Scribner et al. | |
| 5,054,500 A | 10/1991 | Littleford et al. | |
| 5,057,073 A | 10/1991 | Martin | |
| 5,100,424 A | 3/1992 | Jang et al. | |
| 5,117,831 A | 6/1992 | Jang et al. | |
| 5,157,750 A | 10/1992 | Grace et al. | |
| 5,179,961 A | 1/1993 | Littleford et al. | |
| 5,188,632 A | 2/1993 | Goldenberg | |
| 5,203,338 A * | 4/1993 | Jang | 600/463 |
| 5,250,045 A | 10/1993 | Bohley | |
| 5,263,952 A | 11/1993 | Grace et al. | |
| 5,267,993 A | 12/1993 | Grace et al. | |
| 5,304,171 A | 4/1994 | Gregory et al. | |

(Continued)

OTHER PUBLICATIONS

EndoSonics Corporation, Rancho Cordova, Calif., CathScanner I System.

(Continued)

*Primary Examiner* — Ahmed Farah
(74) *Attorney, Agent, or Firm* — Scott J. Hawranek; Sheridan Ross, P.C.

(57) ABSTRACT

Methods of advancing a laser catheter across an occlusion are described. They may include the steps of advancing a guidewire through a first proximal lumen and a distal lumen of the catheter into a first region of the occlusion, retracting the guidewire from the distal lumen, and advancing a diagnostic device from a second proximal lumen of the catheter to examine the occlusion. The methods may also include retracting the diagnostic device from the distal lumen and advancing the guidewire through the distal lumen. The laser catheter may be activated to create a lumen through the occlusion.

24 Claims, 7 Drawing Sheets

U.S. PATENT DOCUMENTS

| | | | | |
|---|---|---|---|---|
| 5,315,614 | A | 5/1994 | Grace et al. | |
| 5,321,783 | A | 6/1994 | Nielson et al. | |
| 5,339,441 | A | 8/1994 | Kardos et al. | |
| 5,352,197 | A | 10/1994 | Hammersmark et al. | |
| 5,364,347 | A | 11/1994 | Jang | |
| 5,383,199 | A | 1/1995 | Laudenslager et al. | |
| 5,400,428 | A | 3/1995 | Grace | |
| 5,412,682 | A | 5/1995 | Laudenslager et al. | |
| 5,415,653 | A | 5/1995 | Wardle et al. | |
| 5,429,604 | A | 7/1995 | Hammersmark et al. | |
| 5,429,617 | A | 7/1995 | Hammersmark et al. | |
| 5,438,587 | A | 8/1995 | Kinley | |
| 5,456,680 | A | 10/1995 | Taylor et al. | |
| 5,458,584 | A | 10/1995 | Ginn et al. | |
| 5,470,330 | A | 11/1995 | Goldenberg et al. | |
| 5,484,433 | A | 1/1996 | Taylor et al. | |
| 5,514,128 | A | 5/1996 | Hillsman et al. | |
| 5,531,700 | A | 7/1996 | Moore et al. | |
| 5,571,151 | A | 11/1996 | Gregory | |
| 5,573,531 | A | 11/1996 | Gregory et al. | |
| 5,596,990 | A | 1/1997 | Yock et al. | |
| 5,620,417 | A | 4/1997 | Jang et al. | |
| 5,643,251 | A | 7/1997 | Hillsman et al. | |
| 5,693,043 | A * | 12/1997 | Kittrell et al. | 606/15 |
| 5,724,977 | A | 3/1998 | Yock et al. | |
| 5,817,144 | A * | 10/1998 | Gregory | 607/89 |
| 5,824,026 | A | 10/1998 | Diaz | |
| 5,836,940 | A | 11/1998 | Gregory | |
| 5,836,946 | A | 11/1998 | Diaz et al. | |
| 5,879,305 | A | 3/1999 | Yock et al. | |
| 5,934,284 | A * | 8/1999 | Plaia et al. | 128/898 |
| 5,935,114 | A | 8/1999 | Jang et al. | |
| 5,976,124 | A | 11/1999 | Reiser | |
| 5,989,243 | A | 11/1999 | Goldenberg | |
| 6,029,671 | A * | 2/2000 | Stevens et al. | 128/898 |
| 6,044,845 | A * | 4/2000 | Lewis | 128/898 |
| 6,117,128 | A * | 9/2000 | Gregory | 606/7 |
| 6,290,668 | B1 | 9/2001 | Gregory et al. | |
| 7,050,692 | B2 | 5/2006 | Harlan et al. | |
| 7,297,154 | B2 * | 11/2007 | Tu et al. | 607/88 |

OTHER PUBLICATIONS

InterTherapy, Costa Mesa, Calif., InterTherapy Modular System Design.

Diasonics, Milpitas, Calif., Interventional Ultrasound System.

Medi-Tech, Inc., Watertown, Mass., designated Ultra-sound Imaging Catheter Catalog No. 01-118.

* cited by examiner

MULTI-PORT LIGHT DELIVERY CATHETER AND METHODS FOR THE USE THEREOF

BACKGROUND OF THE INVENTION

Vascular occlusions restrict the flow of blood to tissue and organs can cause a variety of problems. For example, occlusions that restrict blood flow to the heart can cause heart attacks and angina, and occlusions that restrict blood flow in cerebral blood vessels (e.g., cerebral arteries and veins) can cause strokes and other neurological problems. It is therefore desirable that these occlusions be opened up and removed.

A minimally invasive method of recanalizing an occlusion involves ablating, cutting, pulverizing, dissolving, or otherwise penetrating the occlusion with a vascular catheter. When the catheter reaches the occlusion, a device at the catheter's distal tip is advanced into the occlusion where it performs the operation to cross or penetrate the occlusion. The catheter may also include components that capture, suction or otherwise prevent the occlusion fragments from traveling downstream and creating another blockage.

Advancing the catheter to the site of the occlusion is generally done with the aid of a guidewire that has a smaller distal profile than the catheter itself. Guidewire tips are also designed to be relatively small and stiff so that then can more easily penetrate and advance through the occlusion, providing a path or rail for the subsequently advancing catheter to follow through the occlusion. This process is relatively simple for treating acute occlusions made of relatively soft tissue and occlusions that do not completely block the passage of blood and other fluids through the vessel.

However, another class of occlusions known as chronic total occlusions (CTOs) has been treated less successfully with intravascular catheter procedures. CTOs are generally calcified, fibrotic occlusions that are difficult to penetrate with conventional guidewires. Compounding the problem is that CTOs typically create a complete blockage of the vessel, making it difficult or impossible to flow angiographic contrast agent around the occlusion. This prevents a treating physician from using fluoroscopy, for example, to see a guidewire being advanced into and through the occlusion. Without proper navigation tools there is a significant possibility that the physician may perforate the blood vessel while advancing the guidewire.

The difficult to penetrate nature of CTOs, and the fact that they oftentimes prevent the flow of contrast agent through a vessel have made this class of vascular occlusions difficult to treat with conventional vascular catheters. Successful treatment of CTOs with these devices or methods currently runs about 50 and 60%, with a high risk of blood vessel perforation. Thus, there is a need for new catheter designs and treatment procedures that increase the success rate for successful crossing and recanalization of CTOs.

BRIEF SUMMARY OF THE INVENTION

Embodiments of the invention include methods of advancing a laser catheter across an occlusion. The methods may include the steps of advancing a guidewire through a first proximal lumen and a distal lumen of the catheter into a first region of the occlusion, retracting the guidewire from the distal lumen, and advancing a diagnostic device from a second proximal lumen of the catheter to examine the occlusion. The methods may also include retracting the diagnostic device from the distal lumen, and again advancing the guidewire through the distal lumen to advance the guidewire through the occlusion. The laser catheter may be activated to create a lumen through the occlusion. Additional embodiments include alternatively advancing the guidewire and the diagnostic device a plurality of times through the distal lumen to advance the catheter across the occlusion.

Embodiments of the invention further include additional methods of advancing a laser catheter across an occlusion. The methods may include advancing a guidewire through a first proximal lumen and a distal lumen of the catheter into the occlusion, and retracting the guidewire from the distal lumen and advancing a diagnostic device from a second proximal lumen of the catheter to examine the occlusion. The methods may also include illuminating the occlusion with light emitted from a plurality of optical fibers positioned between the distal lumen and an outside surface of the catheter, where distal ends of the optical fibers terminate at a distal tip of the catheter.

Embodiments of the invention still further include methods of treating an occlusion with a laser catheter. The methods may include the steps of advancing a guidewire through a first proximal lumen and a distal lumen of the catheter into the occlusion, and retracting the guidewire from the distal lumen. The methods may also include illuminating the occlusion with light emitted from a plurality of optical fibers positioned between the distal lumen and an outside surface of the catheter, wherein distal ends of the optical fibers terminate at a distal tip of the catheter. The methods may further include readvancing the guidewire through the distal lumen of the catheter and through the occlusion.

Embodiments of the invention also include catheter assemblies that have a plurality of proximal lumens in a proximal region of the catheter, and a distal lumen in communication with the plurality of proximal lumens. A plurality of optical fibers reside in the catheter and terminate at a distal tip of the catheter. The assembly may also have multiple diagnostic or therapeutic devices in the proximal lumens, where each device can be selectively advanced into the distal lumen.

Embodiments of the invention still further include catheter systems having a catheter body with a proximal end and a distal end. The catheter body may include a proximal region having a plurality of proximal lumens that merge into a distal lumen having a cross-sectional area less than a combined cross-sectional area of the proximal lumens. They catheter body may also include a plurality of optical fibers that reside in the catheter body and terminate at the distal end. The systems may also include a laser-assisted guidewire slidably disposed in a first one of the proximal lumens, and a second guidewire slidably disposed in a second one of the proximal lumens. The laser-assisted guidewire may be slidably advanced from the first proximal lumen through the distal lumen to assist in penetrating the occlusion after the second guidewire, which is used to position the catheter at the treatment site, is retracted from the distal lumen to the second proximal lumen.

Embodiments of the invention may also further include catheter assemblies that have catheters with a proximal section and a distal section. The proximal section may have at least two proximal lumens for component devices (e.g., therapeutic, diagnostic and/or steering devices), and at least one additional proximal lumen that holds a light guide (e.g., optical fibers). The distal section may have a first distal lumen for holding component devices, and another distal lumen for holding the light guide. The light guide may run continuously through the proximal and distal lumens that hold the light guide. The catheter assemblies may further include a first wire and a second wire, where at least a portion of the first wire is removably disposed in a first proximal component lumen, and at least a portion of the second wire is removably disposed in the second proximal component lumen. A portion of a selected one of the first wire and the second wire may be removably disposed in the distal lumen for holding component devices. The first wire may be a guide wire, a laser-assisted guide wire, a steering wire, or an imaging wire, among other types of wires and therapeutic devices. The proximal and distal lumens for holding the light guide may have an annular shape.

Embodiments of the invention still also include methods of removing blood clots and other types of occlusions from a blood vessel (e.g., arterial vessels, cerebral vessels, etc.). The methods may include the step of providing a catheter having a proximal section and a distal section. The proximal section may have at least two proximal lumens for component devices (e.g., therapeutic, diagnostic and/or steering devices), and at least one additional proximal lumen that holds a light guide (e.g., optical fibers). The distal section may have a first distal lumen for holding component devices, and another distal lumen for holding the light guide. The light guide may run continuously through the proximal and distal lumens that hold the light guide. The methods may also include inserting a first guide wire having a distal tip into a first proximal component lumen and the distal component lumen such that a portion of the first guide wire is located in the first proximal component lumen, and another portion of the first guide wire is located in the distal component lumen. The catheter and the first guide wire may be advanced to a first treatment site proximate the clot. Energy may be applied to the clot through the light guide. The first guide wire may be withdrawn so that its distal tip is located in the first proximal component lumen. A laser-assisted guide wire having a distal tip and a light guide may be advanced from a second proximal component lumen through the distal component lumen such that a portion of the laser-assisted guide wire is located in the second proximal component lumen, and another portion of the laser-assisted guide wire is located in the distal component lumen. Energy may be applied to the clot through the laser-assisted guide wire light guide.

Embodiments of the invention may yet further include additional methods of removing an occlusion from a patient's blood vessel. The methods may include the step of providing a catheter having a proximal section and a distal section. The proximal section may have at least two proximal lumens for component devices (e.g., therapeutic, diagnostic, and/or steering devices), and at least one additional proximal lumen that holds a light guide (e.g., optical fibers). The distal section may have a first distal lumen for holding component devices, and another distal lumen for holding the light guide. The light guide may run continuously through the proximal and distal lumens that hold the light guide. A guide wire having a distal tip may be inserted into the catheter such that a portion of it is located in a first proximal component lumen and another portion of it is located in the distal component lumen. The catheter and the guide wire may be advanced to a treatment site proximate the occlusion. The guide wire may be withdrawn such that its distal tip is located in the first proximal component lumen. A steering wire having a longitudinal axis and a bent distal section having a distal tip may be inserted into a second proximal component lumen and advanced though the distal component lumen such that a portion of the steering wire is located in the second proximal component lumen, and another portion of the steering wire is located in the distal component lumen. The steering wire may be rotated about the longitudinal axis while energy is applied to the occlusion through the light guide.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

DETAILED DESCRIPTION OF THE INVENTION

Catheter assemblies, systems and procedures described are designed for crossing intravascular occlusions, including chronic total occlusions (CTOs) that are difficult to penetrate and completely block fluid flow through a vessel. The occlusion is crossed when the guidewire or catheter is moved past the blockage and within the distal lumen of the vessel. This may be accomplished by the rapid exchange of therapeutic (e.g., penetration) and diagnostic devices through the distal end of the catheter that allow a physician to safely navigate a penetrating guidewire or catheter through the occlusion. For example, a procedure may include advancing a penetrating guidewire a safe distance into a CTO before retracting it to a proximal section of the catheter. A diagnostic device (e.g., a optical or ultrasound imaging guidewire) is then advanced through the distal tip of the catheter to allow the physician to know the length and direction of the catheter advancement.

The physician may then activate the laser catheter and penetrate a safe distance into the occlusion, retract the diagnostic device, and advance the penetrating guidewire further through the CTO. Alternation between the guidewire and diagnostic device through the distal tip may be done multiple times before the catheter is activated and advanced to, within, or through the CTO.

The use of diagnostic devices such as ultrasound and/or optical imaging devices allows CTOs and surrounding tissues and vessel walls to be imaged in-situ without requiring that a contrast agent penetrate or surround the occlusion. Thus, a physician or other catheter system operator can use a stiff or energy guidewire to penetrate a calcified, fibrous occlusion with less risk of perforating a vessel wall or other tissue.

The laser catheter assembly is designed for a rapid exchange of devices through the distal lumen of the catheter to provide an efficient "back-and-forth" exchange between a diagnostic device, a guidewire, or some other therapeutic device. This may be accomplished by having multiple lumens (i.e., two or more) in a proximal section of the catheter that have access to a single distal lumen. This allows a relatively short retraction/advancement distance between the proximal lumens and the distal tip of the catheter facilitating the rapid exchange of devices in the catheter.

The devices alternated in the distal lumen of the catheter may include guidewires, diagnostic devices, and therapeutic devices. A diagnostic device may provide the catheter operator with information to locate the positions of device in relation to the occlusion and the vessel walls, among other functions. A therapeutic device may perform actions on the occlusion to help relieve the complete blockage of the vessel by the occlusion, among other functions. Therapeutic devices may also include guidewires and steering wires that help guide at least a portion of the catheter across the occlusion. Diagnostic and therapeutic devices may be exchanged in the distal lumen to advance the catheter across the occlusion and perform actions to recanalize the occlusion.

Additional embodiments of the invention include alternating the advancement of stiff tipped guidewires and soft tipped guidewires through the distal lumen. Stiff-tipped guidewires generally require about 3 grams-force or more to deflect the tip from a straight configuration to a bent configuration, while soft-tipped guidewires require less than 3 grams-force to deflect the guidewire tip. The stiff tipped guidewires may be used to penetrate a length to hard, fibrous material in a CTO while the soft tipped guidewires may help find a path of lower resistance through the occlusion without risk of penetrating the vessel wall. Embodiments also include alternating the advancement of a stiff, bent tipped steering wire with another guidewire. The steering wire allows the redirection of the catheter within the occlusion. It is used to angle the direction of the catheter itself as the distal tip crosses the occlusion. Still additional embodiments include alternating the advancement of a penetrating guidewire and a laser wire to ablate a larger opening in the CTO. Penetrating the opening with the laser wire may be beneficial in situations where soft tipped or stiff tipped guidewires can not penetrate the occlusion.

Embodiments also include the placement of optical fibers eccentric to the distal lumen of the catheter to deliver light to the distal tip while a therapeutic device is present in the distal lumen. The optical fibers may be used to deliver light to the occlusion site for purposes of material ablation, as well as to transmit images from the treatment site.

The optical fibers may extend from an optical coupling element that reversibly couples the optical fibers to a light source, such as an excimer laser. The fibers may traverse the length of the catheter assembly and terminate at the distal end of the catheter. The distal ends of the fibers may be positioned radially around the entire circumference of the distal lumen, or they may partially surround the lumen. For example, the fibers may surround half the distal lumen in a hemispherical distribution. The light transmitted by the optical fibers light energy may be used to ablate or penetrate the occlusion at a treatment site. The fibers may be used to provide images and other information to the catheter operator.

As noted above, the distal lumen is in communication with a plurality of proximal lumens. These proximal lumens may hold multiple therapeutic devices, such as guidewires, laser-assisted guidewires, imaging devices, diagnostic devices, steering wires, and atherectomy devices, among other types of devices. Each of the therapeutic devices may be selectively advanced from one of the proximal lumens into the distal lumen. The first device advanced through the distal lumen may be a guidewire that is used to guide the catheter to the occlusion site. The guidewire may then be retracted back into its proximal lumen, and a second diagnostic device (e.g., a ultrasound imaging wire) advanced from another proximal lumen into the distal lumen. The two devices may be alternated several times to cross a CTO or some other type of occlusion.

A therapeutic device that is no longer needed in the distal lumen only has to be retracted back its proximal lumen in the catheter. The device does not have to be pulled completely out of the catheter to allow a new device to be inserted into the catheter. Thus, a much shorter length of catheter has to be traversed (e.g., the length of the distal lumen) for one therapeutic device to replace another in the distal lumen. This shortens the time and reduces the complexity of an occlusion ablation or crossing procedure compared to conventional catheter assemblies that require the devices to be pulled all the way through the catheter during the procedure.

The assemblies and systems of the invention may also be used to ablate and/or penetrate a surface of the occlusion. This may include using a guidewire to advance the catheter to a site proximate to a surface of the occlusion, and applying light energy from optical fibers surrounding the distal lumen to the occlusion surface. A laser wire advanced through the distal lumen may apply light energy in addition to (or in lieu of) the light from the optical fibers. Following an initial application of light energy, an imaging device may be advanced though the distal lumen to determine the extent of the ablation or penetration and where to further advance the catheter tip (if necessary). Alternatively, a guidewire may be advanced following the initial ablation in an attempt to cross the occlusion.

The guidewire used to position the catheter for ablation may be a steering wire that includes a bent distal portion that can rotate within the catheter and thus produce a bend on the distal tip of the catheter allowing an operator to change the direction of the catheter. Following an application of light energy and advancement of the catheter along the desired path, the steering wire can be retracted and replaced with a guidewire (or another kind of device) to continue the crossing attempt.

Exemplary Catheter Assemblies and Systems

Figures 1, 3:
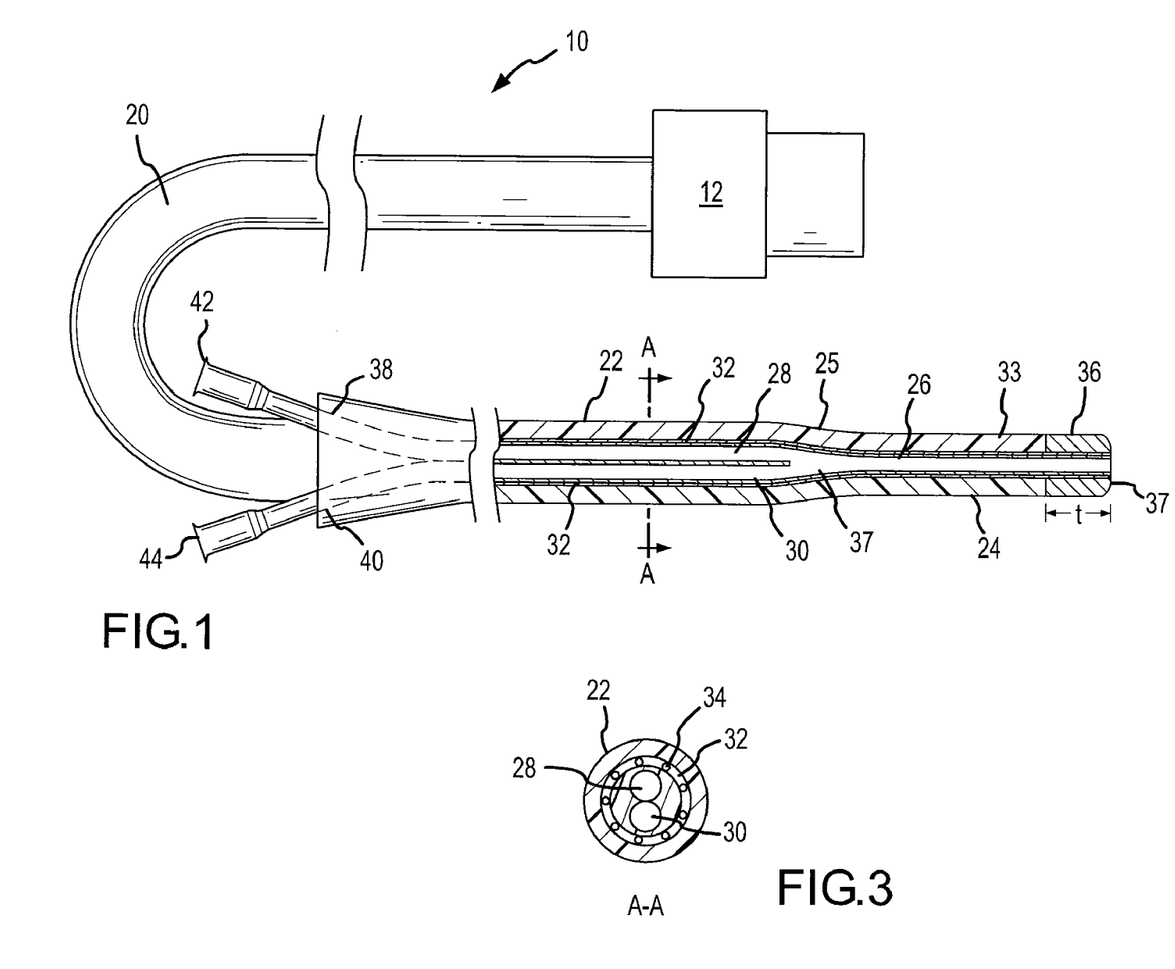
FIG. 1 shows a cut-away side view of a catheter system according to embodiments of the invention.
FIG. 3 shows a cross-sectional view of the catheter in FIG. 1 along the A-A cut line.

Referring now to FIG. 1, a embodiment of a catheter system 10 according to embodiments of the invention is shown. Catheter system 10 includes a catheter with a tail tube 20, a proximal section 22, and a distal section 24. Distal section 24 and proximal section 22 may be cylindrical and may also be interconnected through tapered transition 25 in proximal section 22. System 10 includes a plurality of proximal lumens disposed within the catheter interior, as well as optical fibers for transmitting light energy (e.g., laser light energy) out of the distal tip 37.

The plurality of proximal lumens allow the catheter operator to selectively use and exchange multiple therapeutic devices (e.g., guidewires, laser-assisted guidewires, imaging devices, steering wires, and atherectomy devices, etc.) without having to retract them completely from the catheter. System 10 may also be configured to apply light energy to a treatment site without retracting any of the therapeutic devices from the catheter.

Tail tube 20 may be connected to a coupler 12, which allows the catheter to be connected to a light source (for example an excimer laser). Distal section 24 may optionally be tapered to enhance flexibility and permit the catheter to access narrower vessels. Marker band 36, which may include a radiopaque material, may be provided proximate or flush to distal tip 27. Marker band 36 facilitates visualization of the catheter tip with fluoroscopy. The total length of both the proximal section 22 and distal section 24 may be from about 95 cm to about 185 cm. The length of distal section may range from about 5 to about 40 cm. The catheter shaft will preferably have a length sufficient to permit the catheter to reach from the region where a cut is made to the region where a blood clot is to be removed. For an application where the catheter is to extend from a femoral cut to an occlusion in the heart, the length of the catheter shaft may be, for example, about 135 cm.

The thickness t of marker band 36 may be, for example, about 0.002 in. The outer diameter of distal section 24 may be less than about 0.040 in. Distal section 24 may include a distal lumen 26 and at least partially surrounded by an arrangement of one or more optical fibers 34. In some embodiments, the optical fibers 34 are positioned in an annular shaped, second distal lumen 33 which is eccentrically positioned outside of inner distal lumen 26. The distal lumen 26 may be sized to accommodate a therapeutic device wire, such as a guide wire, laser-assisted guide wire, steering wire, imaging wire, etc., which may be selectively inserted to and withdrawn from the distal lumen 26. The optical fibers 34 may be radially arranged around all or a portion of the distal lumen 26.

Figure 2:
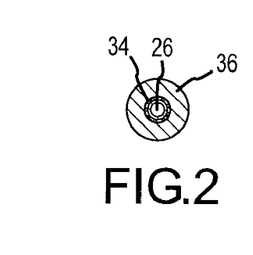
FIG. 2 shows a cross-sectional view of the distal tip of the catheter shown in FIG. 1.

As shown in FIG. 2, the distal lumen 26 may be positioned radially inward of the optical fibers 34. The optical fibers may form a ring between the distal lumen 26 and marker band 36. A variety of additional optical fiber configurations may also be used. The optical fibers may be small-diameter fibers (e.g., about 60 microns in cross-sectional diameter). A plurality of small diameter optical fibers have more flexibility than a single large diameter fiber which allows easier navigation of small and/or tortuous blood vessels.

Referring again to FIG. 1, distal lumen 26 is in communication with multiple lumens in proximal section 22 of the catheter. These include a first proximal lumen 28 and a second proximal lumen 30, both of which are in communication with first distal lumen 26. First proximal lumen 28 and second proximal lumen 30 may be separate lumens until tapered transition region 25 is reached, and the proximal lumens form a single transition lumen 37. Single transition lumen 37 may narrow in a direction from proximal section 22 towards distal section 24 and then may connect to distal lumen 26.

Proximal section 22 of the catheter may be configured to hold a plurality of therapeutic and diagnostic devices. First proximal port 42 is in communication with first proximal lumen 28 and is sized to receive a therapeutic or diagnostic device wire such as a guide wire, a laser-assisted guide wire, a steering wire, an imaging wire, etc., which may be inserted into port 42 and then advanced into first proximal lumen 28. Additional ports (not shown) in communication with first proximal lumen 28 and second proximal lumen 30 may also be provided to facilitate the addition of fluids such as contrast fluids, saline solutions, and clot-busting drugs such as tPA. Similarly, second proximal port 44 may be sized to receive therapeutic devices which may be inserted into port 44 and then advanced through second proximal lumen 30 and distal lumen 26. In the embodiment shown in FIG. 1, insertion branches 38 and 40 are provided and project away from a longitudinal axis of proximal section 22 to facilitate insertion of therapeutic devices from ports 42 and 44 into first and second proximal sections 28 and 30, respectively.

Proximal section 22 is configured to receive a light guide. The light guide may include the plurality of optical fibers 34. Proximal lumen 32 for holding optical fibers may be sized to receive the plurality of optical fibers 34 and may be in communication with tail tube 20. In the catheter embodiments that include distal light guide lumen 33, the proximal lumen 32 may be in communication with the light guide lumen 33 to allow the optical fibers 34 to continuously traverse both lumens.

Optical fibers 34 may be arranged in a variety of configurations with respect the proximal light guide lumen 32. For example, FIG. 3 shows an annular shaped proximal lumen 32. In this example, the two proximal component lumens 28 and 30 are disposed radially inwardly of annular light guide lumen 32. Optical fibers 34 are disposed within the circumference of proximal light guide lumen 32 such that first proximal component lumen 28 and second proximal component lumen 30 are disposed radially inwardly of the fibers as well.

Figure 4A:
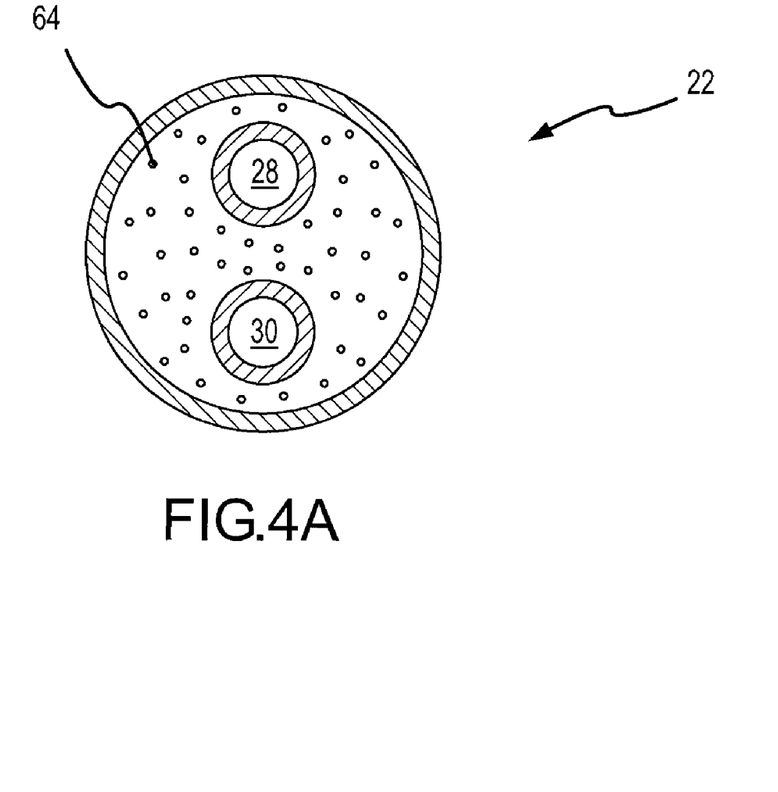
FIG. 4A shows another configuration for a proximal cross-section of a catheter system according to embodiments of the invention.
Figure 4B:
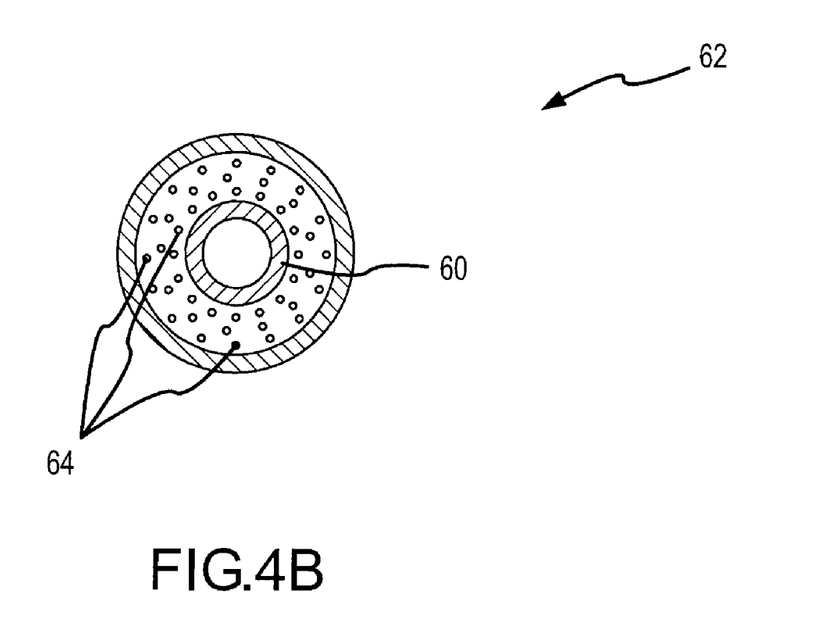
FIG. 4B shows another configuration for a distal tip cross-section of a catheter system according to embodiments of the invention.

FIGS. 4A & B shows additional embodiments of the proximal and distal sections of catheter system 10. FIG. 4A shows a cross-sectional profile of an additional embodiment of the proximal section 22 of catheter 10, where two proximal lumens 28 and 30 are positioned on opposite sides of the center of the catheter. Also bundled within the outer layer of the catheter are a plurality of optical fibers 64 that surround the proximal lumens. The optical fibers 64 may be arranged loosely or close-packed, and may be potted in an epoxy and polished at the distal tip termination.

FIG. 4B shows an embodiment of the distal section 62 extending along catheter 10 from the proximal section 22 shown in FIG. 4A. The distal section 62 includes a round distal lumen 60 at the center of the catheter 10, and the ends of the optical fibers 64 arranged in three annular rows around the lumen 60. The proximal lumens 28 and 30 are both coupled to the distal lumen 60, allowing therapeutic devices (not shown) alternatively to be advanced from one or the other proximal lumen into the distal lumen. One device may be advanced at a time, and the device in the distal lumen 60 may retracted back to its proximal lumen before a device in the other proximal lumen is advanced through the distal lumen. The optical fibers 64 may be arranged loosely or close-packed, and they may be potted in an epoxy and polished at the distal tip termination.

Figure 5A:
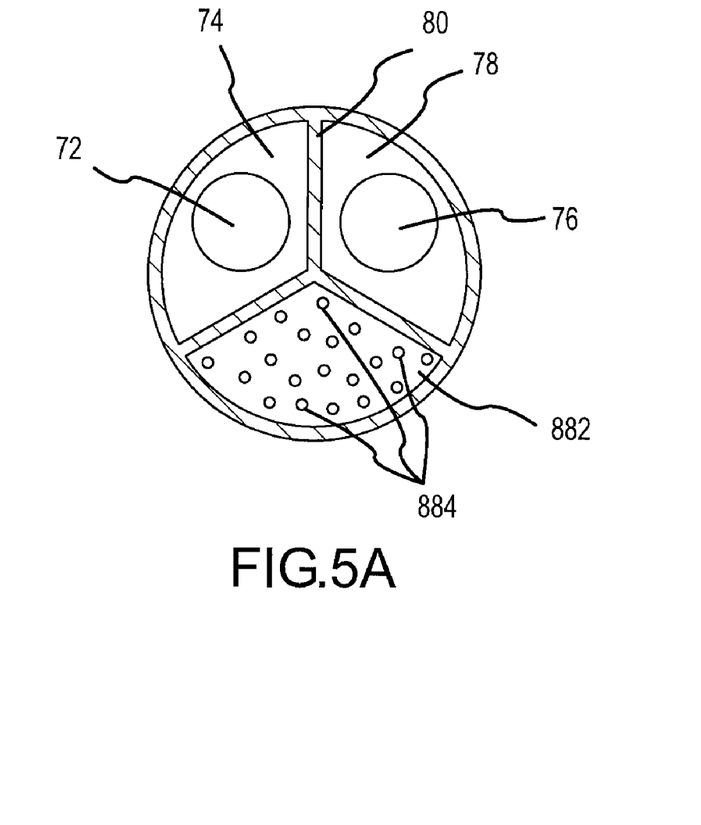
FIG. 5A shows another configuration for a proximal cross-section of a catheter system according to embodiments of the invention.

Referring now to FIGS. 5A&B cross-sections of another embodiment for the proximal section (FIG. 5A) and distal section (FIG. 5B) of the catheter are shown. In this embodiment, the proximal lumens 74 and 78 share at least one common separation wall 80 that keeps the therapeutic devices 72 and 76 separated in the proximal region of the catheter. A third proximal lumen 882 may extend through the proximal and distal sections of the catheter and may contain a plurality of optical fibers 884 that terminate at the distal tip of the catheter.

Figure 5B:
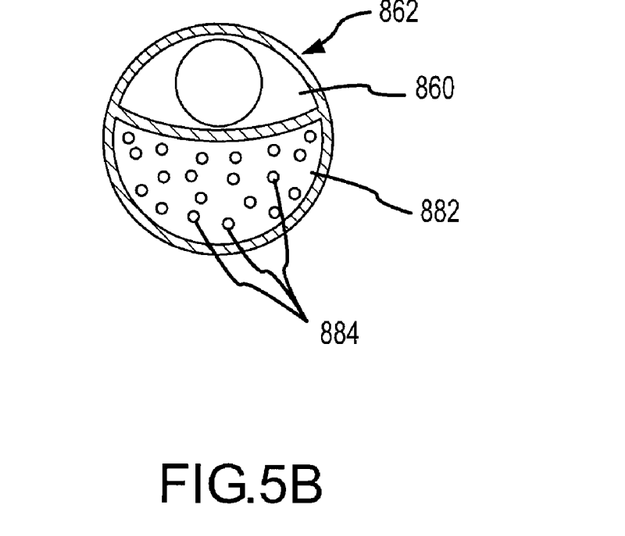
FIG. 5B shows another configuration for a distal tip cross-section of a catheter system according to embodiments of the invention.

FIG. 5B shows a cross-section of the distal section 862 of the catheter that extends from the proximal section shown in FIG. 5A. The distal section 862 includes a first distal lumen 860 that alternately holds the therapeutic devices 72 and 76 from FIG. 8A. The distal section 862 also includes lumen 882 through which the optical fibers 884 in proximal lumen 882 extend to the distal tip of the catheter.

Figure 6:
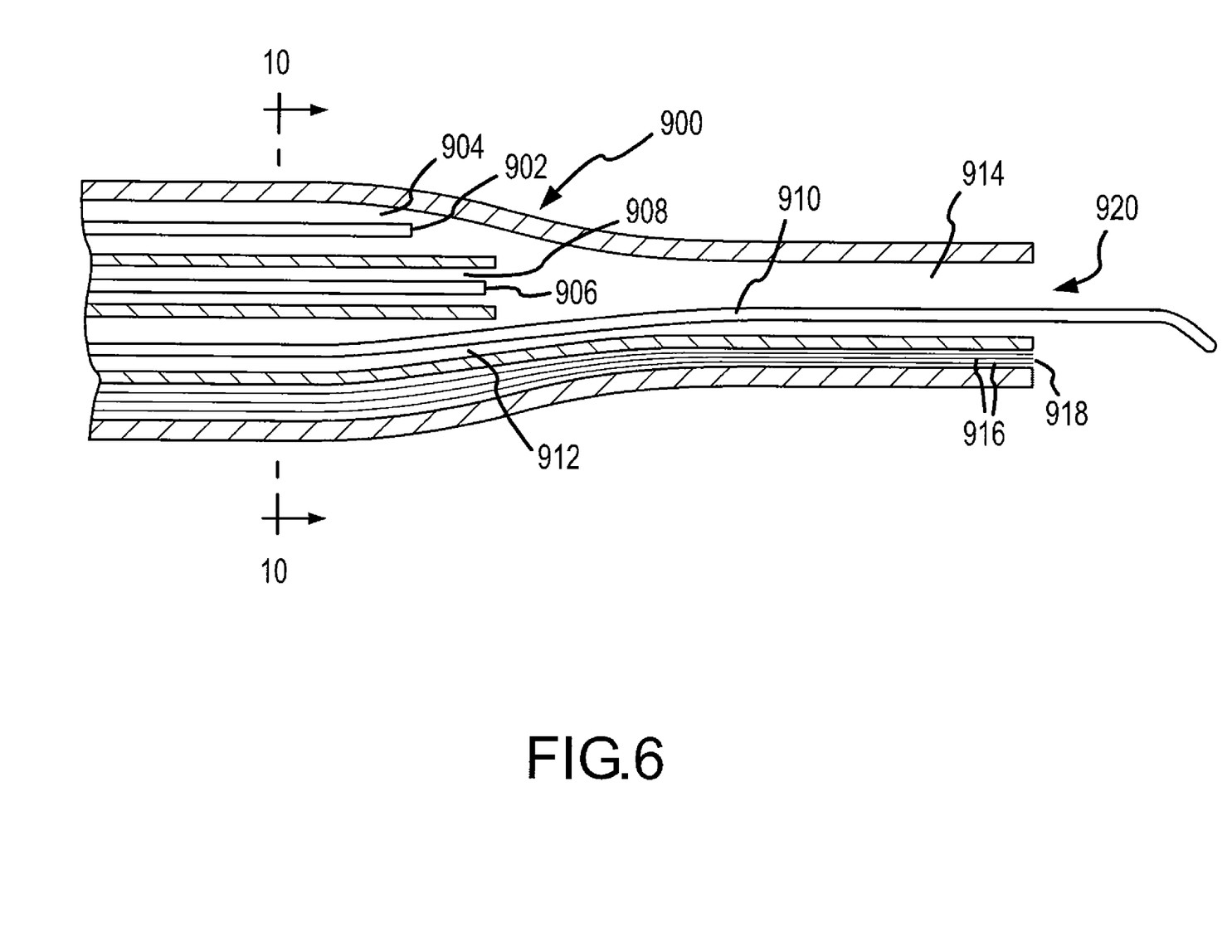
FIG. 6 shows a cut away side view of a distal portion of another catheter according to embodiments of the invention.

Referring now to FIG. 6, a cut away side view of a distal portion 900 of another catheter according to additional embodiments of the invention is shown. The portion 900 includes the distal ends of a first therapeutic and/or diagnostic device 902 in a first proximal lumen 904, a second therapeutic and/or diagnostic device 906 in a second proximal lumen 908, and a third steering wire 910 in a third proximal lumen 912. All three of the proximal lumens are in communication with distal lumen 914 and the therapeutic and/or diagnostic devices held in the proximal lumens may be selectively advanced into and through the distal lumen. The distal portion 900 also shows optical fibers 916 in a lumen 918 adjacent to the third proximal lumen 912. The optical fibers 916 and lumen 918 extend through the proximal and distal sections of the catheter and terminate at the distal section 920 of the catheter. The optical fibers 916 may be fixedly attached to the distal tip via epoxy.

FIG. 6 shows the steering wire 910 occupying distal lumen 914 as well as the third proximal lumen 912. When the distal section of the catheter 920 is moved over the bent part of the steering wire 910, the catheter tip moves in the direction of the bend. The steering wire 910 may be retracted back to the third proximal lumen 912 so that another device (e.g., first or second therapeutic device 902, 906) can be advanced into (and optionally through) the distal lumen 914. Therapeutic and/or diagnostic devices in each of proximal lumens 902, and 906 may be selectively advanced into the distal lumen 914. Embodiments also include the complete removal and replacement of a therapeutic and/or diagnostic device from a proximal lumen with another device as operations are being performed with the other two devices present in the catheter. Embodiments further include increasing the number of proximal lumens in communication with the distal lumen 914 to four, five, six, seven, or more proximal lumens, each of which is operable to hold and advance a therapeutic and/or diagnostic device.

Figure 7:
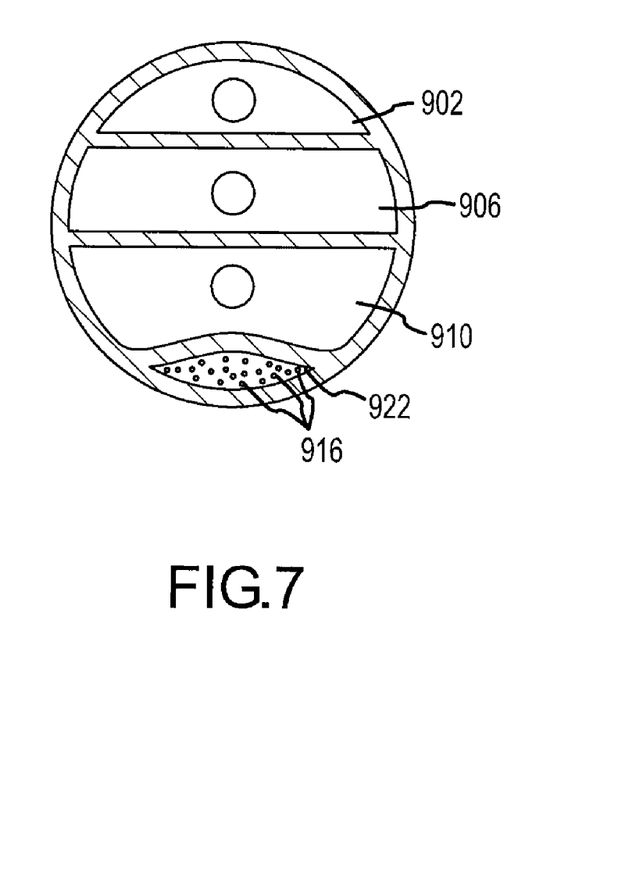
FIG. 7 shows a cross-sectional view of a proximal section of the catheter in FIG. 9 along the A-A cut line according to embodiments of the invention.

FIG. 7 shows a cross-sectional view of a proximal section of the catheter in FIG. 6 along the 10-10 cut line according to embodiments of the invention. The cross-section shows four lumens, including the first, second and third proximal lumens 902, 906, and 910, and a fourth lumen 922 that holds the optical fibers 916.

Figure 8:
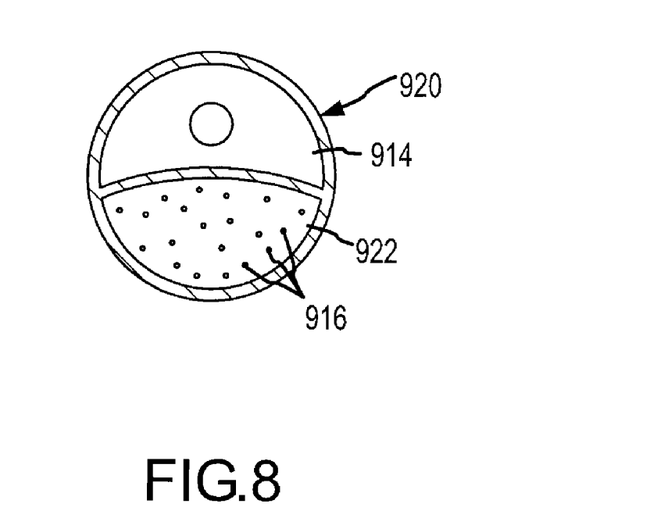
FIG. 8 shows a cross-section view of a distal section of the catheter in FIG. 9 according to embodiments of the invention.

FIG. 8 shows a cross-sectional view of the distal section 920 of the catheter in FIG. 6 according to embodiments of the invention. The distal section 920 may include two lumens, including the fourth lumen 922 from the proximal section of the catheter that extends to the distal section 920, and the distal lumen 914. In the embodiment shown, the optical fibers 916 are grouped in an approximately hemispherical bundle that shares a wall with the distal lumen 914.

Exemplary Methods

Figure 9:
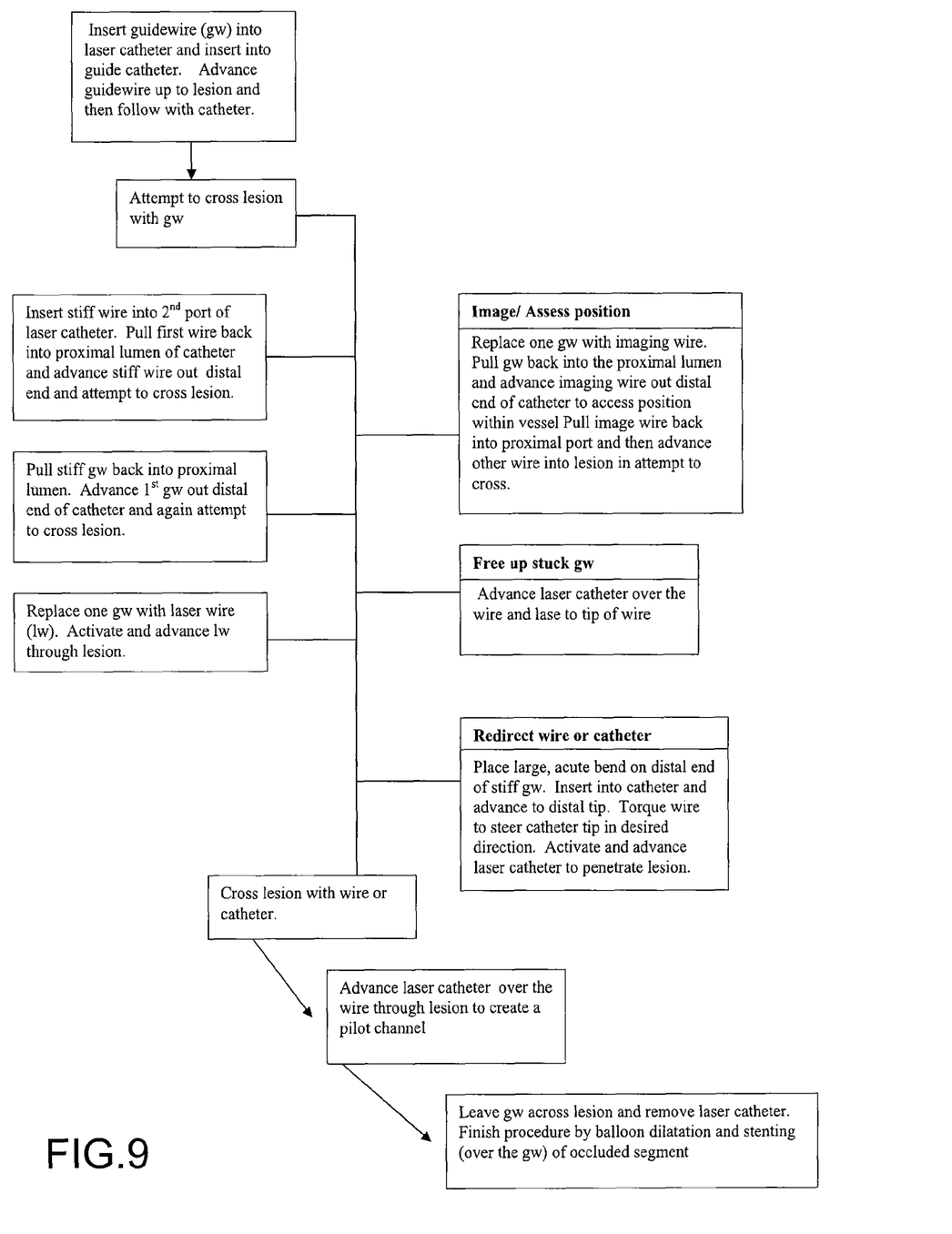
FIG. 9 shows a flowchart of methods of crossing and treating an occlusion according to embodiments of the invention.

FIG. 9 is a flowchart of methods of crossing and treating an occlusion according to embodiments of the invention. The methods may include inserting a guidewire into a guide catheter section of a laser catheter. The guidewire may then be advanced through the catheter to an occlusion, and may be used to help guide the catheter up to the occlusion. The guidewire may then attempt to cross the occlusion in order to help guide the distal tip of the catheter into and possibly through the occlusion.

In many instances where the guidewire is attempting to traverse a chronic total occlusion (CTO) the initial attempt will fail. CTOs are calcified, fibrous occlusions that are difficult for a guidewire to penetrate and traverse in a straightforward manner. Thus, embodiments of the methods shown in FIG. 9 call for retracting the initial guidewire out of the distal lumen of the catheter to a first proximal lumen in the catheter. A stiff tipped guidewire is then advanced from a second proximal lumen through the distal lumen in an attempt to penetrate and cross the occlusion.

It is often the case, however, that the CTO will completely block the passage of blood and other fluids through a vessel, which makes the use of contrast or other types of imaging fluids difficult to use since they typically can only be delivered to one surface of the (e.g., an upstream side surface) of the occlusion. Thus, a physician or other catheter operator would have to advance the stiffed tipped guidewire without navigation aids such a fluoroscopy, which increases the risk of the guidewire perforating the nearby vessel wall or other important tissue.

Thus, the methods in FIG. 9 include retracting the stiff tipped guidewire after a short advancement length into the occlusion and advancing a diagnostic device (e.g., a imaging device such a ultrasound) through the distal lumen of the catheter to assess the advancement of the guidewire through the occlusion. After the operator assesses the best path to advance the guidewire through the occlusion, the diagnostic device may be retracted back to a proximal lumen and the stiff tipped (or different) guidewire advanced from a proximal lumen through the distal lumen to continue the crossing of the guidewire through the occlusion. Alternating between the guidewire and the diagnostic device may be done for several more iterations before the guidewire finally gets across the occlusion.

When the guidewire (either the first guidewire or the stiff tipped guidewire) finally crosses the occlusion, the catheter may be activated and advanced over the guidewire and used to laser ablate a pilot channel in the occlusion. The catheter may then be withdrawn and a new therapeutic device (e.g., a balloon angioplasty device, a stent device, an artherectomy device) may be advanced over the wire through the pilot channel. Once in place through the pilot channel, the therapeutic device may be used to create a large enough opening in the occlusion to permit reasonable blood flow through the vessel.

FIG. 9 also shows some additional steps that may be taken during the process of penetrating and/or opening the occlusion. For example, if the guidewire gets stuck in the occlusion during its advancement, the tip of the catheter may be advanced toward the tip of the guidewire to ablate the occlusion around the tip of the guidewire. The ablation of the occlusion around the guidewire tip should allow the guidewire to become free so that it can be advanced or redirected through the occlusion. The laser light energy is supplied by the optical fibers that terminate at the distal tip of the catheter and transmit laser light (e.g., from an excimer laser) through the length of the catheter.

FIG. 9 also explains how a guidewire with an acute bend on its distal end can be used as a steering wire to steer the distal tip of the catheter in a desired direction into and/or through the occlusion. The bend in the steering wire allows the tip of the catheter to curve conformally with the bend through the occlusion. Embodiments include activating the optical fibers in the catheter tip to oblate a path or pilot channel in the occlusion as the catheter tip is steered through the occlusion by the steering wire.

Figure 10:
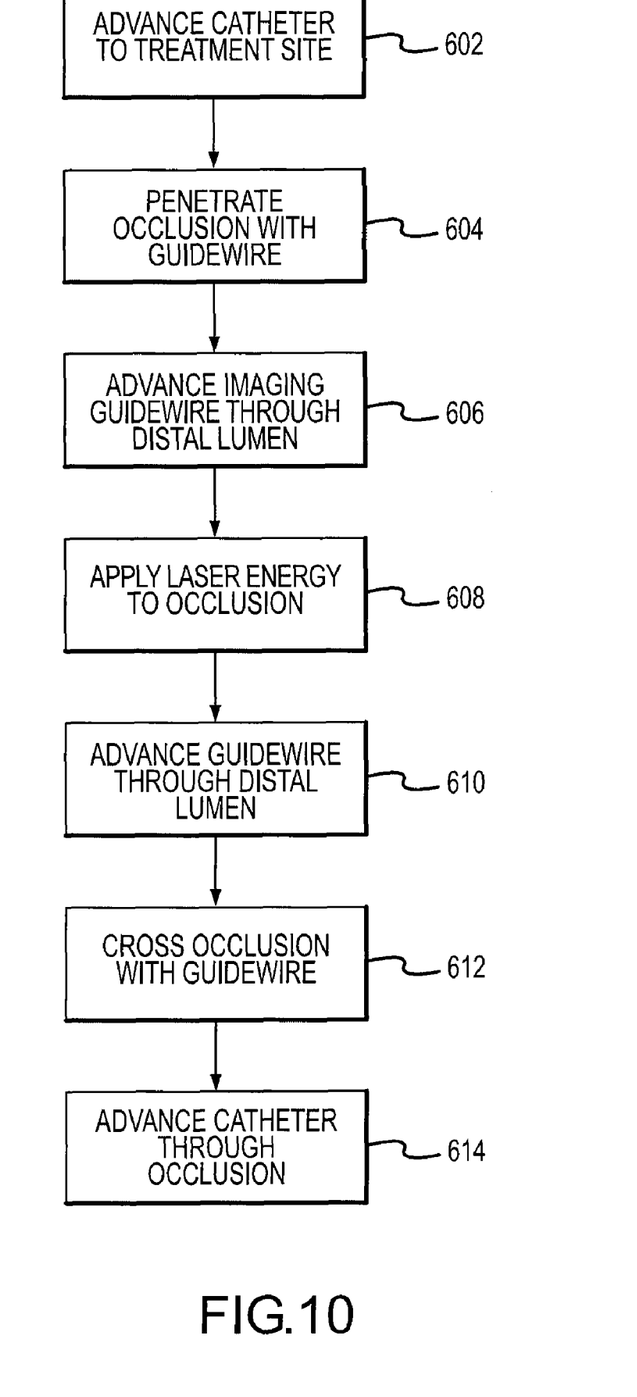
FIG. 10 shows a flowchart of methods of advancing an operating a catheter at a treatment site according to embodiments of the invention.

FIG. 10 is a flowchart illustrating steps in a method 600 of advancing and operating a catheter system according to embodiments of the invention. The method 600 includes advancing the catheter to a treatment site 602 in the patient. This step may involve advancing a guidewire from one of a plurality of proximal lumens in the catheter through a distal lumen. The guidewire may be used to advance the catheter through the patient's body (e.g., through the vascular system of the patient) to the treatment site. The guidewire may also be used to position the distal tip of the catheter in a position to apply light energy from the catheter to a clot or other type of occlusion at the treatment site.

When the guidewire reaches the occlusion the tip of the guidewire may penetrate the occlusion 604 and start to cross it. Penetrating the occlusion may include advancing the guidewire directly into the occlusion as well as sliding the guidewire between the vessel wall and the occlusion to advance the guidewire to the distal lumen of the vessel. After the guidewire penetrates a short distance into the occlusion, it may be retracted from the distal lumen of the catheter to allow an imaging guidewire to be advanced through the lumen 606. The imaging guidewire may be an optical or ultrasonic device allows the catheter operator to visualize and assesses the penetration of the guidewire into the occlusion. The imaging guidewire also helps the operator determine a path to advance of the guidewire through the occlusion without perforating the walls of the vessel.

As the guidewire is advancing across the occlusion, it may be helpful at times to apply laser energy from the catheter to create and/or widen a lumen in the occlusion. This may be done by advancing the tip of the catheter towards the tip of the guidewire and applying laser energy through the optical fibers in the catheter to the occlusion 608. If a laser guidewire is used to supply or help supply the light energy, it may be retracted from the distal lumen to allow the guidewire to readvance back through the distal lumen 610 and into or through the lumen formed in the occlusion.

Alternating between the guidewire and the laser guidewire may be done several times before the guidewire finally crosses the occlusion 612. One the guidewire has crossed the occlusion, the catheter may be activated and advanced through the occlusion 614 to recanalize the occlusion.

Having described several embodiments, it will be recognized by those of skill in the art that various modifications, alternative constructions, and equivalents may be used without departing from the spirit of the invention. Additionally, a number of well known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the lumen" includes reference to one or more lumens and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A method of advancing a laser catheter across an occlusion, the laser catheter comprises a plurality of optical fibers that terminate at a distal end of the laser catheter, the method comprising the steps of:
   advancing a guidewire through a first proximal lumen and a distal lumen of the laser catheter into a first region of the occlusion;
   retracting the guidewire from the distal lumen and advancing a diagnostic device from a second proximal lumen of the laser catheter to examine the occlusion;
   retracting the diagnostic device from the distal lumen and advancing the guidewire through the distal lumen;
   advancing the guidewire through the occlusion; and
   activating the laser catheter to form a lumen in the occlusion.

2. The method of claim 1, wherein the diagnostic device comprises an ultrasound or optical imaging device.

3. The method of claim 1, wherein the guidewire is a soft tipped guidewire.

4. The method of claim 1, wherein the guidewire is a stiff tipped guidewire.

5. The method of claim 1, wherein guidewire and the diagnostic device are each advanced through the distal lumen at least twice to advance the laser catheter across the occlusion.

6. The method of claim 1, wherein the occlusion is a chronic total occlusion.

7. The method of claim 6, wherein the occlusion blocks a flow of fluid through a vessel.

8. The method of claim 1, wherein the plurality of optical fibers are positioned between the distal lumen and an outside surface of the laser catheter.

9. The method of claim 8, wherein the plurality of optical fibers are positioned concentrically around the distal lumen.

10. The method of claim 1, wherein the method further comprises the step of advancing a laser wire through the distal lumen of the laser catheter and ablating a portion of the occlusion.

11. The method of claim 10, wherein the advancing the guidewire step comprises advancing the guidewire through the occlusion at the site of the ablation.

12. A method of advancing a laser catheter across an occlusion, the method comprising the steps of:
   advancing a guidewire through a first proximal lumen and a distal lumen of the laser catheter into the occlusion;
   retracting the guidewire from the distal lumen and advancing a diagnostic device from a second proximal lumen of the laser catheter to examine the occlusion; and
   illuminating the occlusion with light emitted from a plurality of optical fibers positioned between the distal lumen and an outside surface of the laser catheter in a substantially annular configuration, wherein distal ends of the optical fibers terminate at a distal tip of the laser catheter.

13. The method of claim 12, wherein the illuminating the occlusion step ablates at least a portion of the occlusion.

14. The method of claim 13, wherein advancing the guidewire step comprises advancing the guidewire through the occlusion at the site of the ablation.

15. The method of claim 12, wherein the method further comprises the steps of retracting the diagnostic device from the distal lumen and advancing the guidewire through the distal lumen and through the occlusion.

16. The method of claim 12, wherein the method further comprises the step of guiding the laser catheter into the occlusion with the aid of the guidewire.

17. The method of claim 12, wherein the method further comprises the step of advancing a therapeutic device through the distal lumen from a third proximal lumen, wherein the therapeutic device removes at least a portion of the occlusion.

18. The method of claim 17, wherein the therapeutic device comprises a laser-assisted guidewire.

19. A method of treating an occlusion with a laser catheter, the laser catheter comprises a plurality of optical fibers that terminate at a distal end of the laser catheter, the method comprising the steps of:

advancing a guidewire through a first proximal lumen and a distal lumen of the laser catheter into the occlusion;

retracting the guidewire from the distal lumen;

illuminating the occlusion with light emitted from the laser catheter; and readvancing the guidewire through the distal lumen of the laser catheter and through the occlusion.

20. The method of claim 19, wherein the method further comprises the step of advancing a second device from a second proximal lumen of the laser catheter to treat the occlusion.

21. The method of claim 20, wherein the second device is a therapeutic device selected from the group consisting of a laser-assisted guidewire, an anticlotting agent delivery device, and an atherectomy device.

22. The method of claim 19, wherein the illuminating step ablates at least a portion of the occlusion.

23. The method of claim 19, wherein the method further comprises the steps of:

retracting the guidewire from the distal lumen and advancing a diagnostic device from a second proximal lumen of the laser catheter to examine the occlusion;

retracting the diagnostic device from the distal lumen and advancing the guidewire through the distal lumen; and advancing the guidewire through the occlusion.

24. The method of claim 19, wherein the method further comprises the step of guiding the laser catheter into the occlusion with the aid of the guidewire.

* * * * *